United States Patent [19]

Clark

[11] Patent Number: 5,151,425
[45] Date of Patent: Sep. 29, 1992

[54] METHOD OF AND COMPOSITION FOR TREATING INFLAMMATION AND THE IMMUNOLOGICAL RESPONSE THERETO

[76] Inventor: LeaLand L. Clark, 1025 S. 1200 East, Salt Lake City, Utah 84105

[21] Appl. No.: 718,362

[22] Filed: Jun. 20, 1991

[51] Int. Cl.$^5$ ............................................. A01N 43/90
[52] U.S. Cl. ................................... 514/261; 514/886; 514/887
[58] Field of Search ........................ 514/261, 886, 887

[56] References Cited

U.S. PATENT DOCUMENTS 5,021,422  6/1991  Bolund ................................ 514/261

OTHER PUBLICATIONS

Gallmeier "Pavavenous administration of . . . " MMW:121(1):11 1979.

Primary Examiner—Frederick E. Waddell
Assistant Examiner—Gregory Hook
Attorney, Agent, or Firm—Mallinckrodt & Mallinckrodt

[57] ABSTRACT

According to the invention, it has been found that plant cytokinins are effective in treating inflammation in mammals, such as humans. The plant cytokinins are effective to treat the inflammation, to accelerate healing of lesions, and to provide substantially immediate relief of pain, itching, and other immunological responses resulting from inflammation. The plant cytokinin is administered to the mammal in a suitable pharmaceutical preparation.

Particular plant cytokinins which have been tested include trans-zeatin (trans-6-(4-hydroxy-3-methyl(but-2-enyl)-aminopurine)), 6-benzyl-adenine (6-benzylaminopurine), and kinetin (6-furfurylaminopurine).

A composition for topical use in accordance with the method comprises an effective amount of the plant cytokinin in a carrier suitable for topical application to the human skin, for example, hydrophilic ointment, isopropyl alcohol, or a powder formulation. A composition for systemic use, especially oral and parenteral, in accordance with the method comprises an effective amount of the plant cytokinin in a suitable oral or parenteral preparation.

6 Claims, No Drawings

METHOD OF AND COMPOSITION FOR TREATING INFLAMMATION AND THE IMMUNOLOGICAL RESPONSE THERETO

BACKGROUND OF THE INVENTION

1. Field

The invention is in the field of methods and compositions for the treatment of inflammation and the immunological response thereto.

2. State of the Art

Inflammation is a normal body response necessary for repair of damaged tissues and for removal of the irritant or other inflammatory stimulus. The inflammatory response may consist of both humoral and cellular components that generally result in local vasodilatation, increased vascular permeability, edema and cellular infiltration. The inflammation may be accompanied by sensations of burning, stinging, itching, and tenderness.

Steroids, such as cortisone, are among the most potent anti-inflammatory agents currently used. However, steroids have many undesirable and dangerous side effects. It would be desirable to have an anti-inflammatant which is effective, but does not have undesirable side effects.

Plant cytokinins are plant growth regulator substances whose primary effect appear to be to stimulate cell division in plants. However, the plant cytokinins are effective to stimulate cell division in plants only when auxins are present along with the plant cytokinins. Natural plant cytokinins are derivatives of the base adenine while some synthetic plant cytokinins are substituted phenylureas. The use of cytokinins as anti-inflammatory agents has heretofore been unknown.

SUMMARY OF THE INVENTION

According to the invention, it has been found that plant cytokinins are effective in treating inflammation in mammals, such as humans. The plant cytokinins are effective to treat the inflammation, to accelerate healing of lesions, and to provide substantially immediate relief of pain, itching, and other immunological responses resulting from inflammation. The plant cytokinin is administered to the mammal in a suitable pharmaceutical preparation.

Particular plant cytokinins which have been tested include trans-zeatin (trans-6-(4-hydroxy-3-methyl(but-2-enyl)aminopurine)), 6-benzyl-adenine (6-benzylaminopurine), and kinetin (6-furfurylaminopurine).

A composition for topical use in accordance with the method comprises an effective amount of the plant cytokinin in a pharmaceutical preparation suitable for topical application to the human skin, for example, hydrophilic ointment, isopropyl alcohol, or a powder formulation. A composition for systemic use, especially oral and parenteral, in accordance with the method comprises an effective amount of the plant cytokinin in a suitable oral or parenteral preparation.

DETAILED DESCRIPTION OF BEST MODE EMBODIMENTS

In specific embodiments of the invention presently contemplated as the best mode of carrying out the invention in actual practice, a plant cytokinin is administered in various ways to a mammal afflicted with inflammation.

The inflammation may be caused by a variety of events, such as an injury, disease, or infection. In many cases, the inflammation is manifest as a skin lesion. In others, the inflammation is in the joints or internal organs.

If manifest on the skin, an effective amount of the plant cytokinin is prepared using an organic or inorganic solid or liquid carrier and is usually administered topically as a cream using hydrophilic ointment or diluted in isopropyl alcohol or blended in a powder. The patient may also receive the cytokinin by parenteral or oral administration.

Any suitable pharmaceutical preparation of the active compound may be formulated. The process for formulating new drugs into pharmaceutical preparations is well established. See Remington's Pharaceutical Sciences, Managing Ed. J. E. Hoover, 1990, Part 8— Chapters 75–92. The pharmaceutical formulator acquires scientific information about the drug substance which is used to develop optimum dosage forms. Such parameters as crystal size and shape, pH-solubility profile, pH-stability profile, polymorphism, partitioning effect, drug permeability and dissolution behavior are evaluated. Id. at p. 1435.

Various preparations can be formulated for different routes of administration, different strengths, and a variety of other considerations. Among the preparations that may be formulated are: solutions; emulsions; suspensions; extractives; parenteral; intravenous; ophthalmic; so-called "medicated applications" which includes ointments, suppositories, and others; powders; oral solid dosage forms; sustained-release drug delivery systems; and aerosols. Id. at p. xv. It is contemplated that active compounds of the invention will be made into any such forms as desired for particular applications.

Plant cytokinins are nontoxic to mammals and do not appear to have any undesirable side effect. There appears to be no upper limit to the concentration of the cytokinin that may be used in the composition and applied to the skin or otherwise administered to the patient, particularly when applied topically to the skin in the form of an ointment or lotion.

In an animal study, young adult inbred male BL/6 mice weighing approximately 20 g were injected, intraperitoneally with 40, 20, 10 and 5 mg/kg trans-zeatin, obtained from Carolina Biological Supply Company in Burlington, N.C., dissolved in phosphate buffered saline. Five mice were included in each group. Untreated animals were also set aside to serve as controls. Forty-eight hours after injection, the mice were sacrificed, their spleens were removed and processed into a single-cell suspension by passage through a steel mesh. Red blood cells were removed from the cell preparation by the use of hypotonic lysis.

The capacity of splenic T-cells from the mice to respond to various concentrations of PHA was examined in a 72-hr assay. Blastogenic activity was determined with the uptake of tritiated-thymidine following a 12 hour pulse with the radioactive isotope. The cells were harvested with a Titertek Cell Harvester and the amount of radioactivity determined with a Packard Scintillation counter.

A dose-dependent, inhibitory effect of trans-zeatin administration was observed as a decrease in uptake of tritiated-thymidine. This was shown by the progressively higher counts per minute (CPM) with lower doses of trans-zeatin.

Thus, trans-zeatin effected mitogenic response to the T-cell mitogen, PHA. This finding shows that trans-zeatin at the concentrations used has an immunologically suppressive function, i.e., anti-inflammatory function. This test shows that trans-zeatin is an anti-inflammatory agent when administered parenterally. Since trans-zeatin (the best known plant cytokinin) has an effect, it would be expected that the other plant cytokinins would also show similar results.

The animal experiment also suggests a much broader application for the invention. The invention shows an anti-inflammatory effect on white cells (T cells). White cells are known to be involved in systemic as well as topical inflammatory reactions. The term systemic inflammatory reactions, is meant to include the inflammatory diseases attacking organ systems other than the skin. The experiment shows a systemic effect upon systemic, i.e., intraperitoneal, administration of the drug. This suggests a systemic use for the invention.

Wider systemic use is also suggested by the similarities between cytokinins and other systemic anti-inflammatory agents. Steroids and cytokinins have much in common. Just as steroids have utility as topical anti-inflammatory agents in a wide variety of inflammatory conditions, so do cytokinins. Heretofore steroids have been perhaps the most useful agents. Now, the instant invention shows great utility as well. Their wide utility for a variety of skin conditions and their notable effectiveness put them in the same category.

Similarity is also suggested when the mechanism of action of cytokinins is compared with that of the anti-inflammatory steroids. In having an inhibitory effect on white blood cells, cytokinins are similar to steroids. Steroids have also been found useful for treating a wide variety of systemic inflammatory reactions other than topical conditions. Thus, the cited similarities and the experiment strongly suggest that cytokinins could be used to treat all the systemic conditions characterized by an inflammatory reaction that had before been treated by the anti-inflammatory action of steroids.

The need for a safer systemic anti-inflammatory agent is great. One drawback to the use of steroids, especially their systemic use, has been the relatively severe side effects related to their other metabolic effects with long term use. Because cytokinins do not have the other metabolic effects of the steroids, cytokinins should be much safer for long term systemic treatment. Since, the dosages of topical preparations closely approximate the dosages of steroid agents, the dosages of systemic cytokinin preparations would closely parallel the dosages of comparable steroids. Similarly, the systemic dosage form, i.e., parenteral and oral preparations such as tablets, capsules, dose packs, injectables, would parallel the dosage forms of steroids. Thus, systemic dosage forms containing effective amounts of cytokinins are formulated without undue experimentation.

That trans-zeatin demonstrates similar anti-inflammatory results in humans and that other cytokinins also share similar results in humans is supported by several tests on humans, the results of which are described below:

EXAMPLE 1

Patient A suffered from a refractory oral ulcerative lesion, a chronic lichen planus, for many years. After one week of therapy with topical cytokinin, a formulation a 1% benzyl-adenine (obtained from Cabisco Chemicals in Burlington, N.C.) in hydrophilic ointment Patient A noted immediate relief of pain and unprecedented rapidity of healing. Lesions varying from approximately 2-14 mm in diameter, located over the dorsum of the tongue, left buccal mucosa, and right lip virtually disappeared within two weeks.

EXAMPLE 2

Patient B suffered from acne vulgaris on his neck. A 1% preparation of benzyl-adenine in hydrophilic ointment, applied topically, healed all lesions completely within two days. Prior to treatment, the lesions had been present for two weeks.

EXAMPLE 3

Patient C suffered from pigment lesions on her arms for 25 years. Prior to treatment with 1 percent kinetin (obtained from United States Biochemical Corporation), patient was in constant pain of moderate to severe intensity at the pigment site. Patient reported immediate disappearance of pain upon topical application and immediate loss of redness at the lesion site.

EXAMPLE 4

Patient D suffered from atopic dermatitis on her hands for two weeks prior to a topical treatment with 1% preparation of benzyl-adenine in hydrophilic ointment. The patient reported immediate relief from pain and itching at the lesion site. Healing of the lesions occurred 80 to 100 percent more rapidly than with previous treatment.

EXAMPLE 5

Patient E's skin condition of lichen simplex chronicus, on his feet had been present for six weeks prior to administration of benzyl-adenine. Itching disappeared almost immediately upon exposure of the lesion to benzyl-adenine. No previously used treatment relieved patient's itching. Healing occurred about 80 percent more rapidly than with previous medications.

EXAMPLE 6

Patient F suffered from a cold sore of herpes simplex origin on her lip. Upon administration of 1% benzyladenine in hydrophilic ointment U.S.P., patient reported an immediate relief from itching and later reported an 8% decrease in healing time compared to previously used medications.

EXAMPLE 7

Patient G suffered from lesions on her buttocks due to lichen sclerosis et atrophica for about four years. Following topical administration of benzyl-adenine in hydrophilic ointment, patient's lesions showed a 40 percent improvement in healing time as compared to previous medications tried.

EXAMPLE 8

Patient H displayed sweat retention syndrome in atopic eczema on his inner left thigh. Two lesions were selected for the experiment. The control lesion was treated topically with isopropyl alcohol. The test lesion was treated topically with 10 mg trans-zeatin (obtained from Calbiochem in La Jolla, Calif.) in 99% isopropyl alcohol. No change was observed in the control. One and one-half hours later, redness in the trans-zeatin treated lesions was reduced 60 percent, while redness in the control lesions was reduced 10 percent. Subsequent reapplications resulted in a redness reduction of 70% on the trans-zeatin-treated lesion and no change in the control.

EXAMPLE 9

Patient I suffered from severe atopic dermatitis for lifetime, i.e., since 1926, at forearms, shoulders, elbows, hands, and buttocks The instant attack was limited to his forearms. After 3 weeks of therapy with 1% trans-zeatin in hydrophilic ointment, Patient I noted improvement without complete healing. One improvement was elimination of patient's itching and also decreased healing time to about 20% more quickly than usual. Patient usually now itches only when exposed to sunlight or when under stress. Itching was usually moderate, but was eliminated with treatment with trans-zeatin.

EXAMPLE 10

Patient J suffered from Peri-Oral Dermatitis. Perioral dermatitis is extremely resistant to any treatment. After a few weeks of therapy with 1% trans-zeatin in hydrophilic ointment, Patient J noted improvement without complete healing. Trans-zeatin worked well but further follow-up was not possible as patient discontinued visits.

EXAMPLE 11

Patient K suffered from an extremely severe and debilitating combination of Atopic Eczema and Contact Dermatitis for 10 weeks on both hands. Patient's hands were so inflamed that the lesions had replaced his fingerprints after 4 weeks. After 4 weeks of therapy with 1% trans-zeatin in hydrophilic ointment, Patient K's fingerprints grew back. Another improvement was that patient could use his hands. Patient's fingers could again bend and pick up objects. Also, the lesions were completely healed and skin was no longer open and bleeding.

EXAMPLE 12

Patient L suffered from uncomfortable Atopic Eczema for 3 years on the anal area, abdomen, and both arms. After 1 week of therapy with 1% trans-zeatin in hydrophilic ointment, Patient L's lesions were improved, under control, and doing well. Another improvement was that patient reported cessation of itching.

EXAMPLE 13

Patient M suffered from extremely widespread, painful, and inflamed atopic eczema for the patient's entire life on areas of the back and the trunk of the body. Patient noted moderate improvement of lesions after 1 day of therapy with 1% trans-zeatin in hydrophilic ointment. Another improvement was lack of itching and pain within 24 hours. Trans-zeatin worked well, but further follow-up was not possible as patient discontinued visits.

EXAMPLE 14

Patient N suffered from Atopic eczema on the finger tips of both hands. Finger tips were raw. Patient noted up to 80% improvement of lesions after 1 day of therapy with 1% trans-zeatin in hydrophilic ointment. Another improvement was that fingertips were no longer raw and sore.

EXAMPLE 15

Patient O suffered from very severe Herpes Simplex lesions around the mouth almost continuously for 5 years. Patient noted decreased pain and improvement in appearance of lesions after 1 day of therapy with 1% trans-zeatin in hydrophilic ointment. Another improvement was lack of itching and decreased healing time.

EXAMPLE 16

Patient P suffered from extremely severe Herpes Simplex lesions around the lips for 10 weeks. Patient noted decreased pain and improvement in appearance of lesions after 1 hour of therapy with 1% trans-zeatin in hydrophilic ointment. Trans-zeatin worked well, but further follow-up was not possible as patient discontinued visits. However, three refills were made by him through the pharmacy.

EXAMPLE 17

Patient Q suffered from full blown, painful, opensore, Herpes Simplex lesions on the lip for 5 days. Patient noted elimination of pain immediately and clearing of one lesion in two days of treatment with 1% trans-zeatin in hydrophilic ointment Patient noted wonderful improvement. Patient says she usually had suffered with a cold sore 4-5 times a year until this bout and treatment with trans-zeatin.

EXAMPLE 18

Patient R suffered from severe Herpes Simplex lesions on the lips for 3 days. Patient noted elimination of pain immediately and clearing of a first lesion in 1 day. Pain relief was remarkable on the first lesion.

EXMAPLE 19

Patient S suffered from extremely severe Herpes Simplex lesions inside mouth, inside nostrils and down chin for three weeks. Patient noted 80 percent improvement after 6 days and complete healing after 30 days of therapy with 1% percent trans-zeatin in hydrophilic ointment. It was also noted that there was an at least 80% decrease in pain within 15 minutes of application of trans-zeatin 1% in hydrophilic ointment. Neither Zovirax ® or Zelactin ®, two FDA approved drugs for Herpes Simplex, had previously helped pain or healing.

EXAMPLE 20

Patient T displayed severe Peri-Oral Dermatitis. The lesions had been present for several days. Patient noted improvement after the first week of therapy with 1% trans-zeatin in hydrophilic ointment. After the third week of treatment the lesions were gone completely. Also noted was that there was no more scaling, patchiness or soreness of face.

EXAMPLE 21

Patient U had severe atopic eczema. Eczema had been present on the hands for years. Hands were cracked and bleeding on presentment. There was complete healing of the lesions after five days of therapy with 1% trans-zeatin in hydrophilic ointment. It was also noted that pain was completely ameliorated and hands were no longer cracking and bleeding.

EXAMPLE 22

Patient V had uncomfortable Psoriasis. Psoriasis had been present on the scalp for several months. Affected areas were scaling, flaking and itching on presentment. Results were good. There was 90% healing of the lesions after 28 days of therapy with 1% percent trans-zeatin in hydrophilic ointment. Another improvement was lack of scaling and flaking, but there was still some itching.

EXAMPLE 23

Patient W suffered from extremely severe Lichen Planis which had been present on the soles of the feet and palms of hands for 17 years. The affected areas included the soles of feet and palms of hands and were characterized by agonizing, red, swollen, sore, pustular lesions. There was enormous improvement upon treatment with 1% trans-zeatin in hydrophilic ointment within 3 hours. It was further noted that the patient was able to walk, wear her shoes without pain, and regained use of her hands. Subsequent history is not known as Patient W did not return for further follow-up.

EXAMPLE 24

Patient X suffered from severe hyperpigmentation. Pigment had been present on the legs for 7 plus years. The affected areas were characterized by scaling, very dark brown lesions. There was marked improvement of the scaling upon treatment with a mixture of 1% trans-zeatin in hydrophilic ointment and definite improvement of the hyperpigmentation. Patient X was very happy with the improvement.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A method for treating atopic dermatitis and the immunological response thereto comprising administering to a patient in need of such treatment an effective amount of 6-benzyl adenine in a compatible pharmaceutical preparation.

2. A method for treating atopic dermatitis and the immunological response thereto comprising administering to a patient in need of such treatment an effective amount of trans-zeatin in a compatible pharmaceutical preparation.

3. A method for treating lichen simplex and the immunological response thereto comprising administering to a patient in need of such treatment an effective amount of 6-benzyl adenine in a compatible pharmaceutical preparation.

4. A method for treating lichen simplex and the immunological response thereto comprising administering to a patient in need of such treatment an effective amount of trans-zeatin in a compatible pharmaceutical preparation.

5. A method for treating lichen planus and the immunological response thereto comprising administering to a patient in need of such treatment an effective amount of trans-zeatin in a compatible pharmaceutical preparation.

6. A method for treating pigment lesions and the immunological response thereto comprising administering to a patient in need of such treatment an effective amount of trans-zeatin in a compatible pharmaceutical preparation.

* * * * *